(12) United States Patent
Dorn

(10) Patent No.: US 8,075,606 B2
(45) Date of Patent: Dec. 13, 2011

(54) DELIVERY SYSTEM HAVING A RAPID PUSHER ASSEMBLY FOR SELF-EXPANDING STENT, AND STENT EXCHANGE CONFIGURATION

(75) Inventor: Jürgen Dorn, Neulussheim (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 1524 days.

(21) Appl. No.: 10/483,020

(22) PCT Filed: Jul. 4, 2002

(86) PCT No.: PCT/EP02/07435
§ 371 (c)(1),
(2), (4) Date: Mar. 31, 2004

(87) PCT Pub. No.: WO03/003944
PCT Pub. Date: Jan. 16, 2003

(65) Prior Publication Data
US 2004/0199240 A1   Oct. 7, 2004

(30) Foreign Application Priority Data

Jul. 6, 2001 (GB) .................................. 0116599.2
Aug. 31, 2001 (GB) .................................. 0121213.3

(51) Int. Cl.
*A61F 2/06* (2006.01)
(52) U.S. Cl. .................................................... 623/1.11
(58) Field of Classification Search .................. 606/108; 623/1.11, 1.12; 600/585
See application file for complete search history.

(56) References Cited

U.S. PATENT DOCUMENTS 3,485,234 A    12/1969  Stevens
(Continued)

FOREIGN PATENT DOCUMENTS

CA     2449961 A1    1/2003
(Continued)

OTHER PUBLICATIONS

Japanese Patent Office; Corresponding Japanese Patent Application No. 2003-509960; Notification of Reasons for Rejection (English Translation); Jan. 28, 2009; 2 pages.
(Continued)

*Primary Examiner* — Gary Jackson
*Assistant Examiner* — Katherine Dowe
(74) *Attorney, Agent, or Firm* — Rutan & Tucker, LLP

(57) ABSTRACT

A pusher assembly for a delivery system for a self-expanding stent (6) which is delivered by proximal withdrawal of a sheath (4) radially surrounding the stent has a stent pusher element (8) which defines a lumen for a guidewire (2), a pusher strand (16) that extends to the proximal end of the delivery system and bears an end-wise compressive stress during release of the stent. A transfer shaft (12) links the distal end of the pusher strand (16) to the pusher element (8) and lies side-by-side with the guidewire (2). In a rapid exchange version, an adapter (20) provides two lumens side-by-side, one (22) carrying the pusher strand (16) and the other (14) defining a proximal guidewire part. To the adapter is mounted the proximal end of the stent sheath (4). The system allows modular (14) construction, a tapered tip (4A) on the sheath, and an uncluttered internal configuration which facilitates passage of pulses (F) of liquids from the proximal to the distal end of the system.

27 Claims, 7 Drawing Sheets

U.S. PATENT DOCUMENTS

| | | | |
|---|---|---|---|
| 4,580,568 A | 4/1986 | Gianturco | |
| 4,636,346 A | 1/1987 | Gold et al. | |
| 4,759,748 A | 7/1988 | Reed | |
| 4,768,507 A | 9/1988 | Fischell et al. | |
| 4,817,613 A | 4/1989 | Jaraczewski et al. | |
| 4,842,590 A | 6/1989 | Tanabe et al. | |
| 4,950,227 A | 8/1990 | Savin et al. | |
| 4,979,280 A | 12/1990 | Weil | |
| 5,026,377 A | 6/1991 | Burton et al. | |
| 5,061,257 A | 10/1991 | Martinez et al. | |
| 5,085,662 A | 2/1992 | Willard | |
| 5,158,548 A | 10/1992 | Lau et al. | |
| 5,201,757 A | 4/1993 | Heyn et al. | |
| 5,221,372 A | 6/1993 | Olson | |
| 5,234,416 A | 8/1993 | Macaulay et al. | |
| 5,254,107 A | 10/1993 | Soltesz | |
| 5,275,152 A | 1/1994 | Krauter et al. | |
| 5,290,295 A | 3/1994 | Querals et al. | |
| 5,443,477 A | 8/1995 | Marin et al. | |
| 5,445,646 A | 8/1995 | Euteneuer et al. | |
| 5,453,090 A | 9/1995 | Martinez et al. | |
| 5,484,444 A | 1/1996 | Braunschweiler et al. | |
| 5,507,768 A | 4/1996 | Lau et al. | |
| 5,507,769 A | 4/1996 | Marin et al. | |
| 5,522,883 A | 6/1996 | Slater et al. | |
| 5,534,007 A | 7/1996 | St. Germain et al. | |
| 5,571,135 A | 11/1996 | Fraser et al. | |
| 5,571,168 A | 11/1996 | Toro | |
| 5,603,698 A | 2/1997 | Roberts et al. | |
| 5,603,705 A | 2/1997 | Berg | |
| 5,617,900 A | 4/1997 | Weil | |
| 5,618,300 A | 4/1997 | Marin et al. | |
| 5,634,928 A | 6/1997 | Fischell et al. | |
| 5,643,278 A | 7/1997 | Wijay | |
| 5,662,622 A | 9/1997 | Gore et al. | |
| 5,662,703 A | 9/1997 | Yurek et al. | |
| 5,674,208 A | 10/1997 | Berg et al. | |
| 5,683,451 A | 11/1997 | Lenker et al. | |
| 5,690,642 A * | 11/1997 | Osborne et al. | 623/1.11 |
| 5,690,644 A | 11/1997 | Yurek et al. | |
| 5,700,269 A | 12/1997 | Pinchuk et al. | |
| 5,702,418 A * | 12/1997 | Ravenscroft | 623/1.11 |
| 5,707,376 A | 1/1998 | Kavteladze et al. | |
| 5,709,703 A | 1/1998 | Lukic et al. | |
| 5,733,267 A | 3/1998 | Del Toro | |
| 5,738,667 A | 4/1998 | Solar | |
| 5,741,327 A | 4/1998 | Frantzen | |
| 5,772,668 A | 6/1998 | Summers et al. | |
| 5,772,669 A | 6/1998 | Vrba | |
| 5,788,707 A | 8/1998 | Del Toro et al. | |
| 5,792,144 A | 8/1998 | Fischell et al. | |
| 5,792,365 A | 8/1998 | Torini et al. | |
| 5,797,952 A | 8/1998 | Klein | |
| 5,811,043 A | 9/1998 | Horrigan et al. | |
| 5,817,101 A | 10/1998 | Fiedler | |
| 5,824,041 A | 10/1998 | Lenker et al. | |
| 5,910,145 A | 6/1999 | Fischell et al. | |
| 5,951,495 A | 9/1999 | Berg et al. | |
| 5,954,651 A | 9/1999 | Berg et al. | |
| 5,957,930 A | 9/1999 | Vrba | |
| 5,968,052 A | 10/1999 | Sullivan, III et al. | |
| 5,980,533 A | 11/1999 | Holman | |
| 5,984,964 A | 11/1999 | Roberts et al. | |
| 5,993,460 A | 11/1999 | Beitelia et al. | |
| 6,019,778 A | 2/2000 | Wilson et al. | |
| 6,039,749 A | 3/2000 | Marin et al. | |
| 6,042,588 A | 3/2000 | Munsinger et al. | |
| 6,042,589 A | 3/2000 | Marianne | |
| 6,077,295 A | 6/2000 | Limon et al. | |
| 6,080,102 A * | 6/2000 | Konou et al. | 600/114 |
| 6,096,045 A | 8/2000 | Del Toro et al. | |
| 6,126,685 A | 10/2000 | Lenker et al. | |
| 6,143,016 A | 11/2000 | Bleam et al. | |
| 6,146,415 A | 11/2000 | Fitz | |
| 6,152,944 A | 11/2000 | Holman et al. | |
| 6,168,610 B1 | 1/2001 | Marin et al. | |
| 6,168,616 B1 | 1/2001 | Brown, III | |
| 6,177,140 B1 | 1/2001 | Patil et al. | |
| 6,190,393 B1 | 2/2001 | Bevier et al. | |
| 6,206,888 B1 | 3/2001 | Bicek et al. | |
| 6,212,422 B1 | 4/2001 | Berg et al. | |
| 6,217,586 B1 | 4/2001 | Mackenzie | |
| 6,221,081 B1 | 4/2001 | Mikus et al. | |
| 6,228,110 B1 | 5/2001 | Munsinger | |
| 6,238,402 B1 | 5/2001 | Sullivan, III et al. | |
| 6,238,410 B1 | 5/2001 | Vrba et al. | |
| 6,238,430 B1 | 5/2001 | Klumb et al. | |
| 6,241,758 B1 | 6/2001 | Cox | |
| 6,254,608 B1 | 7/2001 | Solar | |
| 6,254,609 B1 | 7/2001 | Vrba et al. | |
| 6,254,611 B1 | 7/2001 | Vrba | |
| 6,264,671 B1 | 7/2001 | Stack et al. | |
| 6,293,966 B1 | 9/2001 | Frantzen | |
| 6,296,622 B1 | 10/2001 | Kurz et al. | |
| 6,306,145 B1 | 10/2001 | Leschinsky | |
| 6,331,186 B1 | 12/2001 | Wang et al. | |
| 6,342,066 B1 | 1/2002 | Toro et al. | |
| 6,350,278 B1 | 2/2002 | Lenker et al. | |
| 6,352,553 B1 | 3/2002 | van der Burg et al. | |
| 6,352,561 B1 | 3/2002 | Leopold et al. | |
| 6,355,060 B1 | 3/2002 | Lenker et al. | |
| 6,361,555 B1 | 3/2002 | Wilson | |
| 6,368,344 B1 | 4/2002 | Fitz | |
| 6,371,979 B1 | 4/2002 | Beyar et al. | |
| 6,375,676 B1 | 4/2002 | Cox | |
| 6,379,365 B1 | 4/2002 | Diaz | |
| 6,380,457 B1 | 4/2002 | Yurek et al. | |
| 6,387,118 B1 | 5/2002 | Hanson | |
| 6,391,050 B1 | 5/2002 | Broome | |
| 6,391,051 B2 | 5/2002 | Sullivan, III et al. | |
| 6,402,760 B1 | 6/2002 | Fedida | |
| 6,413,269 B1 | 7/2002 | Bui et al. | |
| 6,425,898 B1 | 7/2002 | Wilson et al. | |
| 6,432,129 B2 | 8/2002 | DiCaprio | |
| 6,443,979 B1 | 9/2002 | Stalker et al. | |
| 6,468,298 B1 | 10/2002 | Pelton | |
| 6,482,211 B1 | 11/2002 | Choi | |
| 6,488,694 B1 | 12/2002 | Lau et al. | |
| 6,505,066 B2 | 1/2003 | Berg et al. | |
| 6,514,196 B1 | 2/2003 | Sullivan et al. | |
| 6,514,280 B1 | 2/2003 | Gilson | |
| 6,517,547 B1 | 2/2003 | Feeser et al. | |
| 6,517,569 B2 | 2/2003 | Mikus et al. | |
| 6,520,983 B1 | 2/2003 | Colgan et al. | |
| 6,530,947 B1 | 3/2003 | Euteneuer et al. | |
| 6,554,841 B1 | 4/2003 | Yang | |
| 6,572,643 B1 | 6/2003 | Gharibadeh | |
| 6,576,002 B2 | 6/2003 | Dobak, III | |
| 6,579,297 B2 | 6/2003 | Bicek et al. | |
| 6,582,460 B1 | 6/2003 | Cryer | |
| 6,592,569 B2 | 7/2003 | Bigus et al. | |
| 6,599,296 B1 | 7/2003 | Gillick et al. | |
| 6,605,109 B2 | 8/2003 | Fiedler | |
| 6,613,075 B1 * | 9/2003 | Healy et al. | 623/1.11 |
| 6,626,934 B2 | 9/2003 | Blaeser et al. | |
| 6,629,981 B2 | 10/2003 | Bui et al. | |
| 6,629,992 B2 | 10/2003 | Bigus et al. | |
| 6,641,606 B2 | 11/2003 | Ouriel et al. | |
| 6,656,212 B2 | 12/2003 | Ravenscroft et al. | |
| 6,656,213 B2 | 12/2003 | Solem | |
| 6,660,031 B2 | 12/2003 | Tran et al. | |
| 6,663,614 B1 | 12/2003 | Carter | |
| 6,663,666 B1 | 12/2003 | Quiachon et al. | |
| 6,676,666 B2 | 1/2004 | Vrba et al. | |
| 6,676,693 B1 | 1/2004 | Belding et al. | |
| 6,689,120 B1 | 2/2004 | Gerdts | |
| 6,695,812 B2 | 2/2004 | Estrada et al. | |
| 6,695,862 B2 | 2/2004 | Cox et al. | |
| 6,699,274 B2 | 3/2004 | Stinson | |
| 6,702,843 B1 | 3/2004 | Brown et al. | |
| 6,726,712 B1 | 4/2004 | Raeder-Devens et al. | |
| 6,726,714 B2 | 4/2004 | DiCaprio et al. | |
| 6,736,839 B2 | 5/2004 | Cummings | |
| 6,743,219 B1 * | 6/2004 | Dwyer et al. | 604/525 |
| 6,749,627 B2 | 6/2004 | Thompson et al. | |
| 6,773,446 B1 | 8/2004 | Dwyer et al. | |
| 6,780,199 B2 | 8/2004 | Solar et al. | |

| | | |
|---|---|---|
| 6,786,918 B1 | 9/2004 | Krivoruchko et al. |
| 6,790,221 B2 | 9/2004 | Monroe et al. |
| 6,827,731 B2 | 12/2004 | Armstrong et al. |
| 6,830,575 B2 | 12/2004 | Stenzel et al. |
| 6,843,802 B1 | 1/2005 | Villalobos et al. |
| 6,849,084 B2 | 2/2005 | Rabkin et al. |
| 6,858,034 B1 | 2/2005 | Hijlkema et al. |
| 6,860,898 B2 | 3/2005 | Stack et al. |
| 6,866,669 B2 | 3/2005 | Buzzard et al. |
| 6,884,259 B2 | 4/2005 | Tran et al. |
| 6,899,727 B2 | 5/2005 | Armstrong et al. |
| 6,926,732 B2 | 8/2005 | Derus et al. |
| 6,939,352 B2 | 9/2005 | Buzzard et al. |
| 6,942,688 B2 | 9/2005 | Bartholf et al. |
| 6,945,989 B1 | 9/2005 | Betelia et al. |
| 7,001,423 B2 | 2/2006 | Euteneuer et al. |
| 7,025,773 B2 | 4/2006 | Gittings et al. |
| 7,052,511 B2 | 5/2006 | Weldon et al. |
| 7,074,236 B2 | 7/2006 | Rabkin et al. |
| 7,147,657 B2 | 12/2006 | Chiang et al. |
| 7,163,552 B2 | 1/2007 | Diaz |
| 7,172,617 B2 | 2/2007 | Colgan et al. |
| 7,198,636 B2 | 4/2007 | Cully et al. |
| 7,297,302 B2 | 11/2007 | Berg et al. |
| 7,550,001 B2 | 6/2009 | Dorn et al. |
| 2001/0034549 A1 | 10/2001 | Bartholf et al. |
| 2002/0016597 A1 | 2/2002 | Dwyer et al. |
| 2002/0077691 A1 | 6/2002 | Nachtigall |
| 2002/0183826 A1 | 12/2002 | Dorn et al. |
| 2003/0050686 A1 | 3/2003 | Raeder-Devens et al. |
| 2003/0109886 A1* | 6/2003 | Keegan et al. ............... 606/108 |
| 2004/0006380 A1 | 1/2004 | Buck et al. |
| 2004/0015228 A1 | 1/2004 | Lombardi et al. |
| 2004/0073291 A1 | 4/2004 | Brown et al. |
| 2004/0127912 A1 | 7/2004 | Rabkin et al. |
| 2004/0148009 A1 | 7/2004 | Buzzard et al. |
| 2004/0153137 A1 | 8/2004 | Gaschino et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0215229 A1 | 10/2004 | Coyle |
| 2004/0215317 A1 | 10/2004 | Cummings |
| 2004/0254637 A1 | 12/2004 | Yang et al. |
| 2005/0004515 A1 | 1/2005 | Hart et al. |
| 2005/0021123 A1 | 1/2005 | Dorn et al. |
| 2005/0027345 A1 | 2/2005 | Horan et al. |
| 2005/0038493 A1 | 2/2005 | Feeser |
| 2005/0065590 A1 | 3/2005 | Shelso |
| 2005/0065591 A1 | 3/2005 | Moberg et al. |
| 2005/0080476 A1 | 4/2005 | Gunderson et al. |
| 2005/0090890 A1 | 4/2005 | Wu et al. |
| 2005/0149159 A1 | 7/2005 | Andreas et al. |
| 2005/0165352 A1 | 7/2005 | Henry et al. |
| 2005/0209670 A1 | 9/2005 | George et al. |
| 2005/0209672 A1 | 9/2005 | George et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2006/0015171 A1 | 1/2006 | Armstrong |
| 2006/0030923 A1 | 2/2006 | Gunderson |
| 2006/0074477 A1 | 4/2006 | Berthiaume et al. |
| 2006/0085057 A1 | 4/2006 | George et al. |
| 2006/0100686 A1 | 5/2006 | Bolduc et al. |
| 2006/0212105 A1 | 9/2006 | Dorn et al. |
| 2006/0259124 A1 | 11/2006 | Matsuoka et al. |
| 2006/0282152 A1 | 12/2006 | Beyerlein et al. |
| 2007/0055338 A1 | 3/2007 | Dorn |
| 2007/0055339 A1 | 3/2007 | George et al. |
| 2007/0055340 A1 | 3/2007 | Pryor |
| 2007/0055342 A1 | 3/2007 | Wu et al. |
| 2007/0060943 A1 | 3/2007 | Dorn et al. |
| 2007/0060999 A1 | 3/2007 | Randall et al. |
| 2007/0073379 A1 | 3/2007 | Chang |
| 2007/0083256 A1 | 4/2007 | Dorn |
| 2007/0100420 A1 | 5/2007 | Kavanagh et al. |
| 2007/0100422 A1 | 5/2007 | Shumer et al. |
| 2007/0118201 A1 | 5/2007 | Pappas et al. |
| 2007/0118206 A1 | 5/2007 | Colgan et al. |
| 2007/0179519 A1 | 8/2007 | Huisun |
| 2007/0191864 A1 | 8/2007 | Shumer |
| 2007/0191865 A1 | 8/2007 | Pappas |
| 2007/0191925 A1 | 8/2007 | Dorn |
| 2007/0219624 A1 | 9/2007 | Brown et al. |
| 2010/0179637 A1 | 7/2010 | Dorn et al. |

FOREIGN PATENT DOCUMENTS

| | | |
|---|---|---|
| DE | 199 36 059 A1 | 2/2001 |
| DE | 10201151 A1 | 7/2003 |
| EP | 0 221 570 | 11/1986 |
| EP | 0380873 A2 | 8/1990 |
| EP | 0 436 303 A1 | 7/1991 |
| EP | 0505686 A1 | 9/1992 |
| EP | 0 564 894 A1 | 10/1993 |
| EP | 0 611 556 A1 | 8/1994 |
| EP | 0 630 657 A1 | 12/1994 |
| EP | 0 699 451 A2 | 3/1996 |
| EP | 0941716 | 9/1999 |
| EP | 1084728 A1 | 3/2001 |
| EP | 1 095 634 A2 | 5/2001 |
| EP | 1488763 A2 | 12/2004 |
| GB | 0114939.2 | 6/2001 |
| JP | 1150516 A | 6/1989 |
| JP | 11505162 T | 5/1999 |
| JP | 11313893 | 11/1999 |
| JP | 11313893 A | 11/1999 |
| JP | 2004-530507 T | 10/2004 |
| JP | 3725550 | 12/2005 |
| WO | WO 96/36298 | 11/1996 |
| WO | 9639998 A2 | 12/1996 |
| WO | 9707756 A1 | 3/1997 |
| WO | WO 98/12988 A1 | 4/1998 |
| WO | WO 98/14224 | 4/1998 |
| WO | WO 99/25280 A1 | 5/1999 |
| WO | WO 99/44541 A1 | 9/1999 |
| WO | WO 99/47075 A1 | 9/1999 |
| WO | WO 99/51167 A3 | 10/1999 |
| WO | WO 00/00104 A1 | 1/2000 |
| WO | WO 00/71059 A1 | 11/2000 |
| WO | WO 00/78248 A1 | 12/2000 |
| WO | WO 01/17458 | 3/2001 |
| WO | WO01/34061 | 5/2001 |
| WO | WO 01/34061 A1 | 5/2001 |
| WO | WO-0134061 A1 | 5/2001 |
| WO | 0164134 A1 | 9/2001 |
| WO | 0215820 A2 | 2/2002 |
| WO | 02087470 A1 | 11/2002 |
| WO | WO 02/102279 | 12/2002 |
| WO | 03002019 A2 | 1/2003 |
| WO | WO 03/002020 | 1/2003 |
| WO | 03030783 A1 | 4/2003 |
| WO | 2004062458 A2 | 7/2004 |
| WO | 2005053574 A2 | 6/2005 |

OTHER PUBLICATIONS

Sep. 14, 2009 Office Action in Japanese patent application No. 2003-509960.

Oct. 26, 2009 Japanese Office action in Japanese patent application No. 2006-500573.

PCT/EP2002/007435 filed on Jul. 4, 2002 Preliminary Report on Patentability mailed Jan. 20, 2003.

PCT/EP2002/007435 filed on Jul. 4, 2002 Search Report mailed Jan. 23, 2003.

PCT/EP2002/011082 filed on Oct. 2, 2002 Preliminary Report on Patentability mailed Jan. 7, 2004.

PCT/EP2002/011082 filed on Oct. 2, 2002 Search Report mailed Jan. 24, 2003.

PCT/EP2004/000248 filed on Jan. 15, 2004 Preliminary Report on Patentability mailed Jul. 15, 2005.

PCT/EP2004/000248 filed on Jan. 15, 2004 Search Report mailed Nov. 22, 2004.

PCT/EP2004/000248 filed on Jan. 15, 2004 Written Opinion mailed Nov. 11, 2004.

PCT/EP2004/013339 filed Nov. 24, 2004 Preliminary Report on Patentability dated Apr. 1, 2007.

PCT/EP2004/013339 filed on Nov. 24, 2004 Search Report mailed Oct. 7, 2005.
PCT/EP2004/013339 filed on Nov. 24, 2004 Written Opinion mailed Oct. 7, 2005.
PCT/EP2007/063347 filed Dec. 5, 2007 Written Opinion mailed Jun. 10, 2009.
PCT/EP2007/063347 filed on Dec. 5, 2007 Preliminary Examination mailed Jun. 10, 2009.
PCT/EP2007/063347 filed on Dec. 5, 2007 Search Report mailed Feb. 4, 2008.

* cited by examiner

DELIVERY SYSTEM HAVING A RAPID PUSHER ASSEMBLY FOR SELF-EXPANDING STENT, AND STENT EXCHANGE CONFIGURATION

TECHNICAL FIELD

This invention relates to a stent pusher assembly, and to a delivery system having a rapid-exchange configuration for deploying a self-expanding stent at a stenting site within a human or animal body.

BACKGROUND AND CONTENT OF THE INVENTION

EP-A-1 095 634 (EP 634) discloses all features of the preamble of independent claims 1 and 11. EP 634 discloses a system in which the soft atraumatic distal tip of the system is at the leading end of the inner catheter. The outer sheath of the delivery system has a distal end which stops proximally short of the atraumatic tip.

Stents to be deployed at a stenting site within a human or animal body expand radially in the course of delivery, from a radially compact delivery disposition to a radially larger deployed disposition. In self-expanding stents made of stainless steel, the deformation of the stent is below the elastic limit, the stent until its deployment being radially confined and under elastic stress and typically released by proximal withdrawal of a confining sheath while the stent is itself prevented from moving proximally with the confining sheath by abutment with a stop on the distal end of a catheter shaft which suffers axial compressive stress while the surrounding sheath is proximally withdrawn.

By contrast, stainless steel stents which are relaxed in a radially compact disposition suffer plastic deformation when expanded into their deployed disposition by inflation of a balloon within the lumen of the stent.

An early example of stainless steel self-expanding stents is Gianturco U.S. Pat. No. 4,580,568 and an early example of the balloon expansible stainless stent is Palmaz EP-A-221 570.

A third category of stent is the memory metal stent, made of a biologically compatible nickel-titanium shape memory alloy with martensitic and austenitic phases. At body temperature, the stent "seeks" to revert to the austenitic phase. Typically it is confined within a surrounding sheath and again released at the stenting site by proximal withdrawal of this sheath.

The present invention offers improvements in systems to deliver those stents which are brought to the stenting site within a confining surrounding sheath.

In the technical field of stenting, there is a desire to reduce the transverse dimensions of the stent delivery system. In this field, the widely used measure of transverse cross-section is the unit of "French", often abbreviated to "F" which is a one third part of a millimeter. Thus, a 6F (six French) delivery system has a diameter of 2 millimeters.

For any particular stenting operation, one has to select a particular stent and a particular delivery system. There is a large choice in both of these elements. Accordingly, it would be an advantage for manufacturers of stents and their delivery systems to achieve a degree of modularity in the design and construction of stents and their delivery systems. For example, there is a wide range of stents which could be delivered by a six French delivery system and it would therefore be convenient for the manufacturer of a stent delivery system to be able to tailor a basic six French system to fit any particular stent which would be compatible with a six French delivery system. This would reduce costs, to the advantage of patients, while retaining full flexibility for medical practitioners to optimise their choice of stent for any particular patient.

Like many catheter systems, a stent delivery system is often used with a flexible guidewire. The guidewire is preferably made of metal, and is slidably inserted along the desired body passage. The delivery system is then advanced over the thus pre-placed guidewire by "backloading" or inserting the proximal end of the guidewire into a distal guidewire port leading to a guidewire lumen defined by the delivery system.

Many conventional delivery systems define guidewire lumens that extend along the entire length of the outer sheath. These delivery systems are described as "over-the-wire" delivery systems, in that the delivery system is guided to the site of the stenosis over the guidewire, the guidewire thereby exiting the delivery system at the proximal end of the delivery system. "Over-the-wire" delivery systems provide several advantages, including improved trackability, the ability to flush the guidewire lumen while the delivery system is inside the patient's body, and easy removal and exchange of the guidewire while the delivery system remains in a desired position in the patient.

In some circumstances, however, it may be desirable to provide a "rapid exchange" delivery system, which offers the ability more easily to remove and exchange the delivery system while retaining the guidewire in a desired position within the patient. In a rapid-exchange delivery system, the guidewire occupies a lumen located only in the distal portion of the delivery system. The guidewire exits the delivery system through a proximal guidewire port, closer to the distal end of the delivery system than to its proximal end, and extends in parallel along the outside of the proximal portion of the delivery system.

Because a substantial length of the guidewire is outside the delivery system, it may be manually held in place close to the point where it passes the entry point on the body of the patient, as the delivery system is removed. This facilitates handling, removal and exchange of the delivery system for the practitioner for the following reasons.

With a guidewire lumen that is much shorter than the full catheter length a single physician can insert and remove a stent delivery system into and from the patient's body. Whereas over-the-wire delivery systems require a guidewire having a length at least double the length of the outer catheter, the rapid-exchange configuration allows the use of much shorter guidewires which enable a single physician to handle the proximal end of the guidewire at the same time as the catheter at the point of its entry into the body of the patient.

Accordingly, the present invention advantageously provides a stent delivery system having a rapid-exchange configuration for delivering and deploying a self-expanding stent.

Stents themselves cannot be directly seen during their journey to the stenting site, nor can one directly see whether the stent is exactly located as desired within the stenting site. Rather, indirect means have to be used to follow the progress of the stent through the body and make sure that it is correctly located before it is deployed. Thus, a stent delivery system is used during deployment to carry radiopaque contrast or marker fluid to the stenting site so that the target stenosis can be seen through the reduced amount of radiopaque fluid in the bodily lumen at the stenosis. This radiopaque fluid is generally injected through an injection port at the proximal end of the delivery system and through an annular space between an outer sheath of the delivery system and a proximal portion of an inner catheter shaft. The visibility of the stenosis is adversely affected when the lumen, through which radiopaque contrast fluid is injected, is too small to deliver a strong pulse of contrast fluid. As pulses of fluid are used for visualisation, the effectiveness of visualisation depends on the volume flow in each pulse. This in turn depends on the ease of flow of the fluid along the full length of the delivery system, from the point of injection at the proximal end, to the stenosis beyond the distal end of the delivery system.

Thus, delivery systems which offer a large cross-section and unimpeded lumen for contrast fluid will be favoured by radiologists, other things being equal. The visibility can additionally be increased by further reducing the resistance of the system to pulses of contrast fluid. It is therefore an object of the present invention to provide good visualisation with contrast fluid, without sacrifice of other important performance aspects of the delivery system, including pushability and low overall diameter. By increasing "pushability" we mean the capability to be advanced longer distances along narrower and more tortuous bodily lumens.

Furthermore, the delivery system invariably carries at least one radiopaque marker at a known location relative to the length of the stent, so that radiologists can be sure of the location of the ends of the stent, on the basis of their knowledge of the location of the radiopaque marker. Even if the stent is rendered sufficiently radiopaque for it to be seen, it is still useful to have a radiopaque marker on the distal end of the delivery system, to reveal successful separation of the stent from the delivery system.

Thus, in our example of a six French delivery system, to be used for delivering stents of various lengths, there will be a wish to provide radiopaque markers within the delivery system at two spaced-apart locations on the axis of the delivery system, corresponding to the opposite ends of the stent (until the stent is deployed out of the system). One object of the present invention is to offer a degree of modularity in this design aspect.

With delivery systems having a rapid-exchange configuration, just as with over-the-wire systems, the stent delivery system is advanced over the guidewire, itself normally within a guide catheter, in order to bring the distal tip and stent to the stenting site. Depending on the application, different diameter guidewires are specified. Two commonly used guidewire diameters are 0.46 mm/0.018 inches and 0.89 mm/0.035 inches (commonly known as 18 thou or 35 thou guidewires). Thus, a further degree of modularity can be achieved by offering a delivery system which is compatible with a range of guidewire diameters, specifically, both 18 thou and 35 thou guidewires.

It would be an advantage for any new stent delivery system to be able straightforwardly to take the place of those previous delivery systems which individual practitioners have grown to be comfortable using. One such system uses in its proximal portion a metallic rod, which can be either solid or hollow, made of stainless steel.

Good design for stent delivery systems is indicated by manufacturing steps which can be performed with high precision and reliability, yet with acceptable cost levels. This is yet another objective of the present invention.

Finally, for any system which is extremely long in proportion to its diameter, and features at least three co-axial elements, the cylindrical surfaces of these co-axial elements need to be so composed and conformed that friction between them is low enough that the co-axial elements can be moved tolerably easily axially relative to each other. It is yet another object of the present invention to provide systems which enable bringing these friction levels down to advantageously low levels.

Another consideration when a self-expanding stent is released progressively by successive proximal stepwise movements of the outer confining sheath results from the delivery system typically being extremely long in proportion to its cross-sectional dimensions, and constructed predominantly or wholly from synthetic polymeric materials which have substantial elasticity and marked kinetic aspects to their deformation characteristics. In such a case, any particular rate of strain imposed on the proximal end of the outer sheath is likely to be experienced at the distal end of the same sheath in a somewhat different strain rate. For example, a fast squeeze of the trigger of a deployment system at the proximal end of the sheath will likely result in a somewhat slower resulting proximal advancement of the distal end of the same sheath. Furthermore, a pull on the sheath will impose compressive stresses along the length of the inner shaft, likely leading to a proximal movement of the stent which then relaxes back to the original, more distal, position of the stent as the tensile stress in the outer sheath eases back towards zero. In its own delivery systems, present applicant has observed what happens at the distal end of a stent delivery system during successive squeezes of the trigger of a delivery system which pulls the outer sheath proximally in a series of steps. The appearance at the stent end of the system is as if the system were "breathing" in that it, and the stent, moves axially first proximally, then distally, with each squeeze of the trigger.

This "breathing" phenomenon is of course a complicating factor when it comes to precision of placement of the stent within any particular stenting site. It is yet another object of the present invention to ameliorate this problem.

SUMMARY OF THE INVENTION

According to one aspect of the present invention there is provided a pusher assembly for a delivery system for a self-expanding stent, the pusher assembly constituting a catheter shaft with a proximal pusher end to receive an end-wise compressive force and a distal pusher end to deliver said force to a stent to be delivered, the pusher assembly comprising a pusher strand extending from the proximal pusher end to a distal strand end which is nearer the distal pusher end than the proximal pusher end; a pusher element which abuts the stent in use to deliver said force to the stent; and a transfer shaft having a proximal and a distal end, the proximal end being connected to the distal tube end and the distal end being connected to the pusher element and characterised in that the pusher element defines a guidewire path, and the transfer shaft lies to one side of said path.

By contrast, in earlier systems such as that of EP 634 in which the atraumatic tip is carried on the inner catheter, the pusher element is mounted on a tube which has a guidewire lumen and extends distally all the way to the tip.

According to another aspect of the present invention, there is provided a stent delivery system having a rapid exchange configuration for a self-expanding stent which provides improved visualisation through an increased volume flow in each pulse. The volume flow in each pulse is increased in the present invention due to a simplified and reduced internal structure of the delivery system.

The scheme of a simplified delivery system is represented in FIG. 1 which shows the essential features of a basic delivery system including an outer sheath 4 confining the stent 6 in a radially compressed state and a pusher element 8 preventing proximal movement of the stent when the outer sheath 4 is proximally withdrawn. The pusher element is carried on an inner catheter shaft 3. Here, the delivery system is inserted over a guidewire 2 into a lumen of a human or animal body.

In one of its aspects, the present invention employs a short inner catheter shaft so that its distal end is relatively close to the proximal guidewire lumen exit port. In conventional delivery systems, the inner catheter shaft 3 extends beyond the distal end of the stent 6 to provide a tapered tip, for ease of insertion of the delivery system into the patient's body and for reducing trauma whenever the catheter is advanced distally. Above-mentioned EPO 634 discloses a stent delivery system which conforms to this conventional model.

In the present invention, using the pusher element to define at least a short distal guidewire lumen, and providing the system tip taper on the distal end of the outer sheath, renders redundant an inner catheter within the stent and distal of the stent. Therefore, the internal structure of the delivery system is more open, which consequently enhances ease of flow and the volume of contrast fluid that can be ejected from the distal end of the delivery system with each successive pulse imposed from the proximal end of the delivery system. Hence, visualisation is improved.

In another aspect of the invention the manufacturing and assembling steps required to get the delivery system of the present invention ready for use are minimised due to the simplified internal structure. There exists no longer the need for keeping the stent at a fixed position on the inner catheter shaft while the outer sheath is fitted over the stent. Also, the risk of advancing the stent too far distally and out of the distal opening of the outer sheath during assembly of the delivery system is minimised, since the outer sheath in the present invention comprises the tapered tip which acts as a distal stopper for the stent during assembly.

The introduction of a stent using the stent delivery system of the present invention, and subsequent removal of the delivery system, is facilitated especially in tortuous vessels and other body lumens having a relatively narrow diameter because, once the stent has been placed at a desired site inside the patient's body, there need be no component of the delivery system which is radially inwardly located from the stent and which has to be proximally withdrawn through the stent lumen. Especially in narrow and sharply curved body vessels, this might introduce a risk that the distal tip being withdrawn through the stent lumen interferes with bodily tissue protruding radially inwardly through the interstices of the stent and into the stent lumen. The delivery system of the present invention avoids this problem by providing the tapered tip on the distal end of the outer sheath so that, during removal of the delivery system out of the patient's body, there need be no system components which travel proximally within the stent lumen and are likely to engage with the inner surface of the stent.

In one preferred embodiment, the pusher element is a cylinder which has a distal-facing end face at the distal end of the cylinder to push on the proximal end of the stent. Thus, the end face will likely be flat and transverse to the axis of the cylinder. The pusher element can serve as, and preferably does serve as, a radiopaque marker.

If desired, the pusher element can also serve as a mount for a distal marker carrier tube cantilevered distally forward from the pusher element to lie within the space that will correspond to the lumen of the stent to be deployed by the system. This is useful when it is required to have on the delivery system a radiopaque marker for the distal end of the stent. This radiopaque marker can be placed on the carrier tube at a position at or towards the distal end of the carrier tube and corresponding to the distal end of the stent. For stents of different lengths, the length of the carrier tube can easily be varied to correspond to the stent length, prior to fixing the distal marker on the carrier tube.

It will be appreciated that the carrier tube requires relatively little strength, so can be made thin and flexible, thereby reducing the risk of its interfering with tissue protruding through the stent during its withdrawal from the stenting site.

As the carrier tube is a relatively simple and isolated part of the delivery system, and conveniently made of a synthetic polymeric material, it will be a relatively simple matter to change the length of the carrier tube to suit any particular stent destined to be carried on the system. If desired, the carrier tube can be extended backwardly proximally from the pusher element and given a bell end or flared end outwardly proximally. This flared end provides security against the possibility of unwanted distal slippage of the carrier tube distally through the pusher element and of being left behind in the body when the delivery system is withdrawn. It may also be useful to guide the guidewire through the system whenever there is need to introduce the distal end of the guidewire from the proximal end of the system.

In yet another aspect of the invention, the modular construction of the delivery device results in fewer steps during manufacturing and assembly of the stent delivery system. The device may be modularized by using a transfer shaft connecting the rod or inner catheter with the pusher element. This can be set to any desired length, to accommodate stents of different length in a delivery system which features standard length catheter components such as the sheath, rod or inner catheter and pusher tube. It may be convenient to use a welded joint to fasten one or both of the two ends of the transfer shaft to the pusher element and rod, respectively.

For a better understanding of the various aspects of the present invention, and to show more clearly how its several features can be carried into effect, individually or in selected combinations reference will now be made, by way of example, to the accompanying drawings of embodiments of the present invention.

DETAILED DESCRIPTION OF THE PREFERRED EMBODIMENTS

The following description of the preferred embodiments of the present invention is merely illustrative in nature, and as such does not limit in any way the present invention, its application, or uses.

Figure 1:
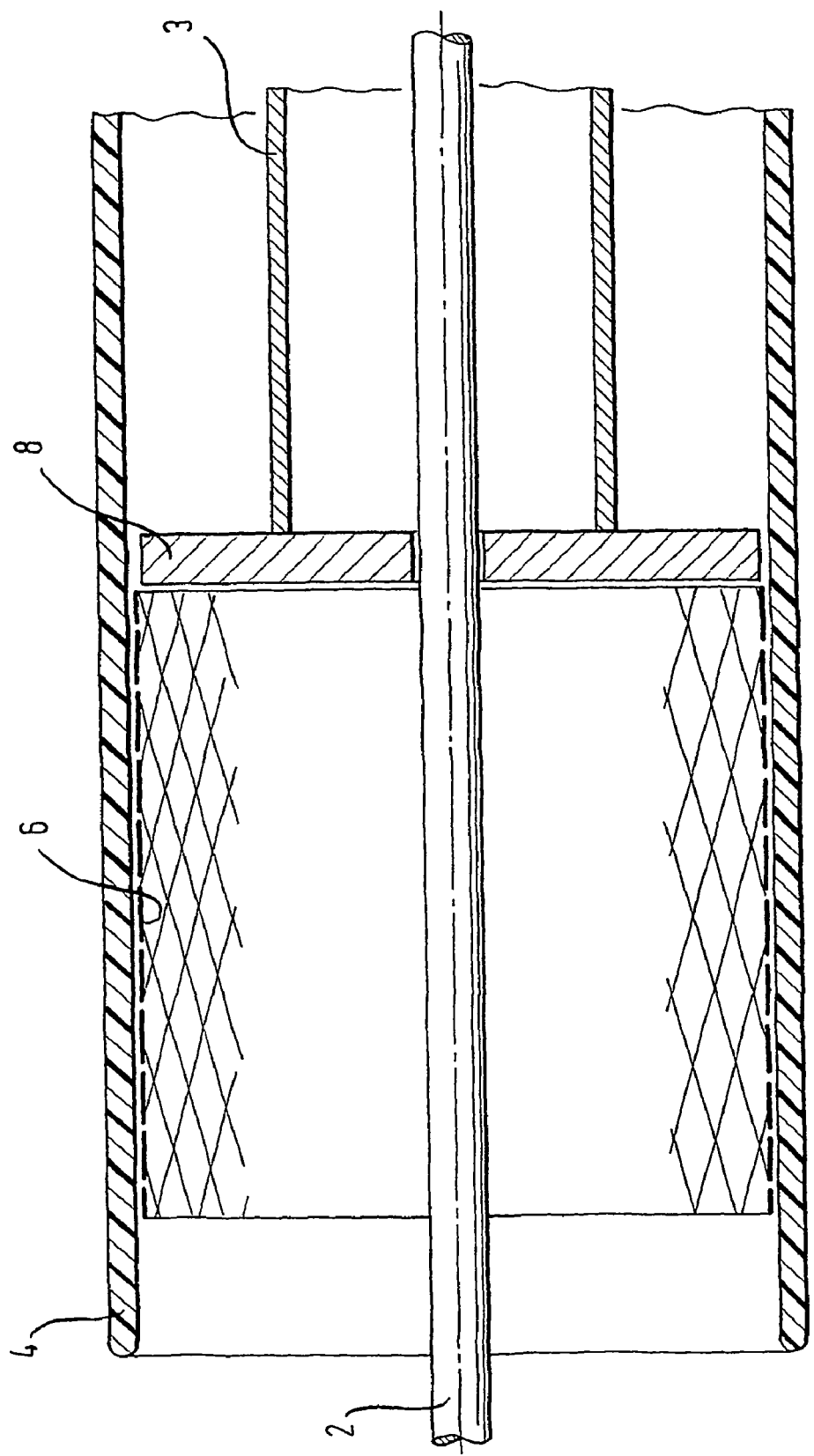
FIG. 1 shows in longitudinal axial section the distal portion of a prior art delivery system.
Figure 2:
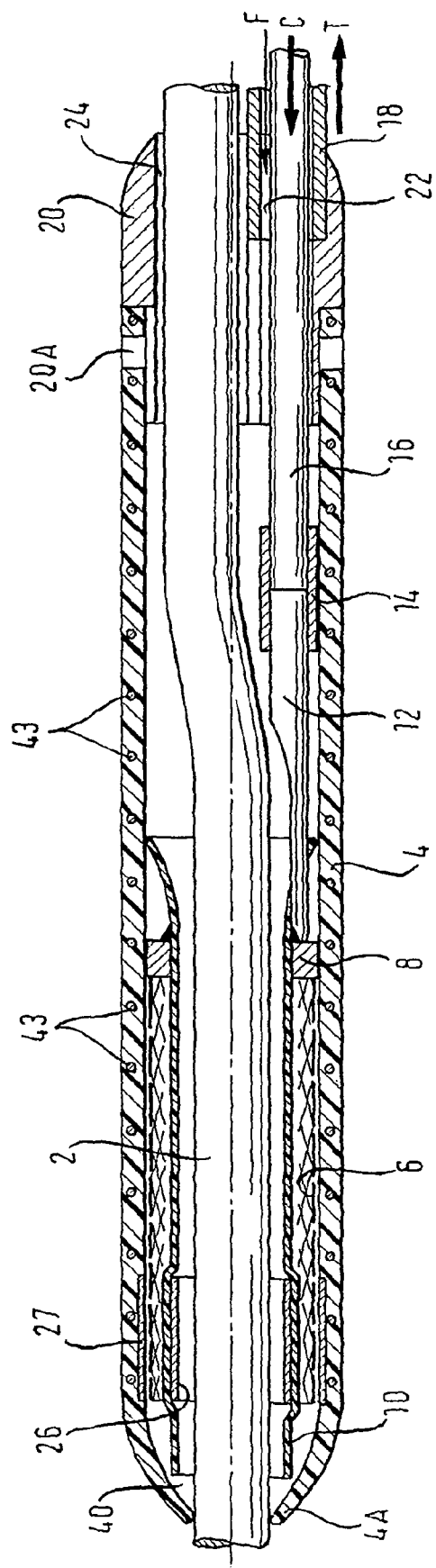
FIG. 2 is a cross-section of the distal portion of a delivery system having a rapid-exchange configuration in accordance with a preferred embodiment of the present invention.

FIG. 2 shows a cross-section of the distal portion of a delivery system having a rapid-exchange configuration in accordance with a preferred embodiment of the present invention.

In FIG. 2, a guidewire 2 extends beyond the distal end of the distal portion of the delivery system along which the stent delivery system is advanced to the site of the stenosis inside the patient's body. The stent 6 is held in a radially compressed state by means of an outer sheath 4 the distal end of which constitutes the distal end of the stent delivery system. The distal tip 4A of the outer sheath 4, as shown in FIG. 2, is tapered in order to facilitate advance of the stent delivery system along a bodily lumen. Furthermore, the outer sheath 4 comprises a radiopaque marker 27 the position of which is indicative for the distal end of the stent until deployment of the stent. The guidewire 2 extends all the way through the outer sheath lumen and exits the distal portion of the stent delivery system at a proximal guidewire port 24.

A pusher element 8 abutting the stent 6 in use of the delivery system prevents proximal movement of the stent 6 when the outer sheath 4 is withdrawn proximally to release the stent. The pusher element 8, which at the same time serves as a proximal radiopaque marker, is connected to a transfer shaft 12. The pusher element 8 is preferably laser-welded to the distal end of the transfer shaft 12. For ease of connection the distal end of the transfer shaft 12 is tapered and embedded in a respective slot provided in the proximal end of the pusher element 8. The distal end of the transfer shaft 12 is tapered, and the transfer shaft 12 is corresponding oblate at its distal end, so that the distal end of the transfer shaft 12 can be fitted into a respective slot of the adjacent pusher element 8, with the circumferential surface over a specific arc length of the oblated end being flush with the circumferential surface of the pusher element 8. The slot provided in the proximal end of the pusher element 8 has an axial length which extends from the proximal end of the pusher element 8 beyond midway along the axial length of the pusher element 8. This ensures a sufficiently rigid connection of the transfer shaft 12 with the pusher element 8. Such shaping of the distal end of the transfer shaft 12 and the pusher element 8 optimises the flow of injected contrast fluid F, since the fluid does not meet any unnecessary barrier when travelling along the length of the transfer shaft 12. In this way, the flow resistance of the injected contrast fluid F is minimised.

The transfer shaft 12 is capable of receiving an endwise compressive force C and transmitting the force C to the proximal end of the stent 6, thereby preventing proximal movement of the stent 6 when the outer sheath 4 is withdrawn proximally by imposition of tensile force T on the sheath 4. The arrows in FIG. 2 are indicative for the direction of the respective forces T and C.

A connection piece 14, such as a tube, at the proximal end of the transfer shaft 12, as shown in FIG. 2, enables the accommodation of different stent lengths in an unchanged sheath 4 by an appropriate adjustment in the length of the transfer shaft 12 in accordance with the length of the respective stent 6.

The cut-to-length transfer shaft end within the connection tube 14 is glued or soldered to the connection tube 14. The proximal end of the transfer shaft 12 is directly connected to the distal end of the rod 16 by means of a solder joint or glue. Otherwise, the connection tube 14 can be no more than a collar into which two adjacent ends of separate transfer shaft portions are inserted end-to-end and approximated, such that both abutting ends of the transfer shaft 12 portions are in physical contact with each other inside the collar. Therefore, there is no relative axial movement of the two adjacent ends of the transfer shaft 12 portions within the collar. Thus, the longitudinal force transmission between the proximal end of the tube 16 receiving the endwise compressive force C to the proximal end of the stent 6 is optimised.

The proximal end of the distal portion of the stent delivery system, as shown in FIG. 2, comprises an adaptor 20 having two lumens 22, 24 for effecting the rapid-exchange configuration. The guidewire 2 exits the distal portion of the stent delivery system through a guidewire port 24 of the adaptor 20, so as to be exposed outside the stent confining sheath 4 to enable the rapid exchange. The guidewire port 24 is preferably off-centre of the adapter 20. The orifice of the second lumen 22 is defined by a pipe 18.

Referring to FIG. 2, a rod 16 being part of the pusher assembly and preferably made of metal abuts at a distal end thereof the proximal end of the transfer shaft 12 inside the connection piece 14. Its proximal end extends beyond the proximal end of the pipe 18. The rod 16 extends distally from the distal portion of the delivery system through the second lumen 22 of the adapter. At its proximal end it receives the endwise compressive force C.

In a further embodiment of the present invention, not shown, the rod 16 can be provided as a tube with a lumen running from the proximal end of the system to the lumen of the pipe 18.

In both embodiments, the pipe 18 is connected to the adaptor 20 and furthermore, the adaptor 20 is connected to the outer sheath 4. The integrity of this connection is somewhat crucial for the proper functioning of the delivery system, since the outer sheath 4 is usually made of a polymeric material whereas the adaptor 20, the rod 16 (or tube), and the transfer shaft 12 are preferably made of metal, such as stainless steel. Metal-to-polymer connections are normally made by means of an adhesive.

Figure 3:
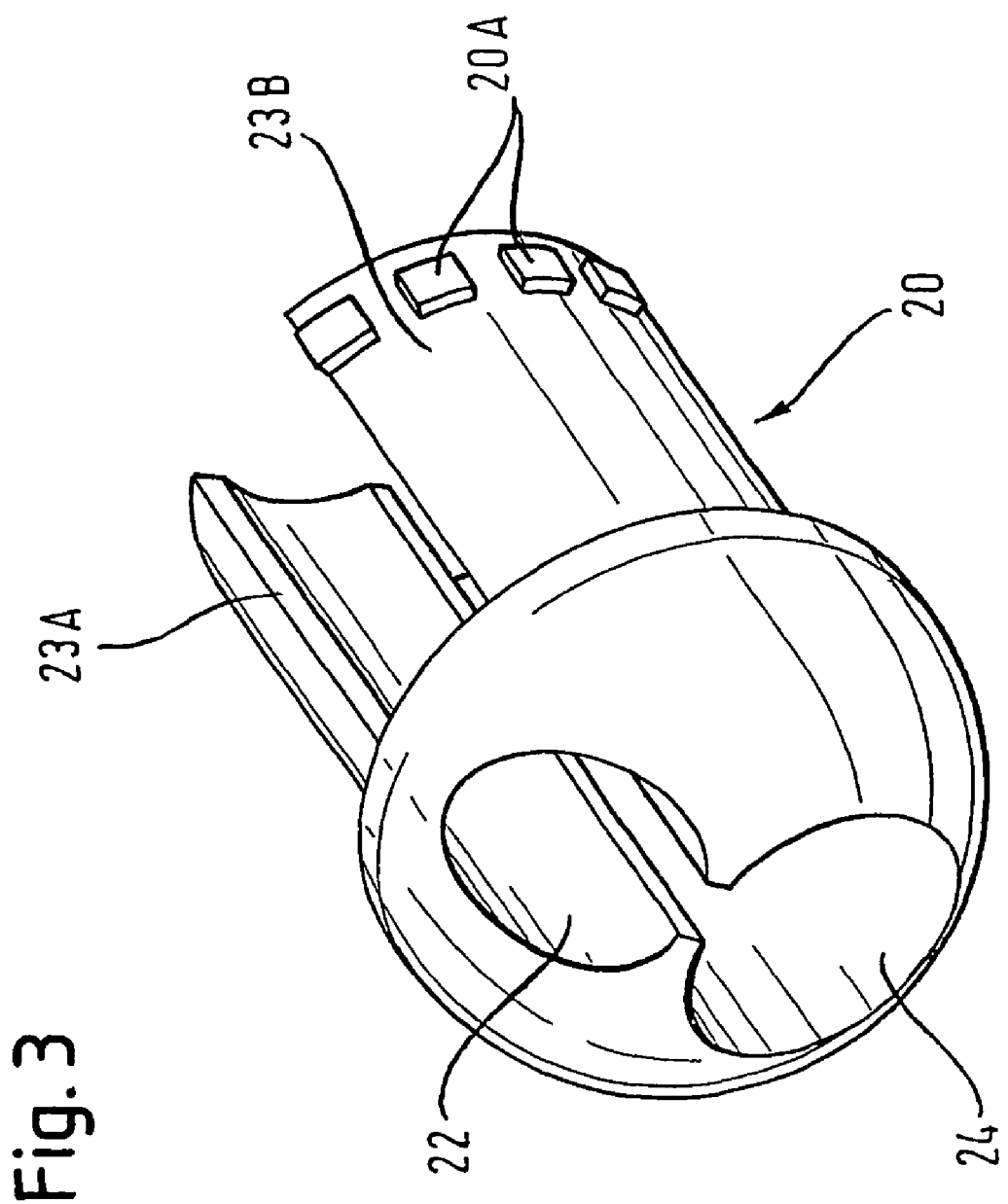
FIG. 3 shows an isometric view of the adapter having two lumens effecting the rapid exchange configuration.

To permit sufficient rigidity and to provide a rupture-resistant connection of the pipe 18 through the adaptor 20 to the outer sheath 4, the pipe 18 is advantageously welded into a recess of the adaptor 20. Tension studs 20A, as shown in FIG. 3, are provided in the proximity of the distal end of the adapter 20 to engage along the entire circumference of the adapter 20 with individual strands of a braid 43 encapsulated by the polymeric material of the outer sheath 4. The tension studs 20A protrude radially outwardly into the interstices of the braid 43 to reduce the dependence on glue to prevent rupture of the connection between the adapter 20 and the outer sheath 4. The stud to braid link between the pipe 18 and the outer sheath 4 via the adapter 20 feature metal all the way from one end of the system to the other so that the risk that the adhesive joint between the adapter 20 and the outer sheath 4 may break is reduced and the strain suffered by the system in releasing a stent is also kept small. Other type of connections will be apparent to those skilled in the art and an explicit explanation thereof is therefore omitted.

When using the stent delivery system, a tensile force T acts on the pipe 18, thereby proximally displacing the outer sheath 4 to release the stent 6, and at the same time a compressive force C is received by the tube or the rod 16 at its proximal end and is transmitted to the transfer shaft 12 in order to prevent proximal displacement of the stent 6 during stent deployment.

Since the pusher element 8 provides a lumen for the guidewire, abuts the stent 6 in use and is supported axially by the transfer shaft 12, and since the stent 6 is self-expanding and so is pressing radially outwardly on the sheath 4, there is no need for an inner catheter to extend beyond the proximal end of the stent 6. The tapered tip 4A of the sheath 4 facilitates advance of the catheter system through a tortuous lumen of the patient's body. The tapered tip 4A also resists inadvertent or premature distal movement of the stent 6 relative to the sheath 4, such as when the delivery system is introduced into a narrow vessel inside the patient's body. In this way, the tapered tip 4A of the outer sheath 4 can act a distal stopper for the stent.

For a detailed description of such tapered tips and their use, see Applicant's WO 01/34061.

A distal marker carrier 10, itself carried on the pusher element 8, exhibits a length sufficient to project distally beyond the stent 6 and defines a lumen for the guidewire 2. In use, the guidewire 2 extends along an axial path which lies side by side with the transfer shaft 12, which shaft 12 is off the axis of the outer sheath 4. The proximal end of the distal marker carrier 10 is attached, conveniently by glue, to the inner surface of the pusher element 8 to fix its axial position. The proximal end of the distal marker carrier 10 has a flared end or shows some sort of tulip-shape which facilitates distal advancement of the guidewire 2 through the pusher assembly of the delivery system. The fixing established by the glue and the flared ends also reduces the likelihood of separation of the carrier tube 10 from the pusher element 8.

The distal marker carrier 10 carries a distal marker 26, such as a radiopaque marker, indicating the position of the distal end of the stent 6. The inner surface of the distal marker 26 is flush with the inner surface of the distal marker carrier 10 for undisturbed elative axial movement of the guidewire 2. Preferably, a particular heat treatment is employed to attach the distal marker 26 to the distal marker carrier 10, so that the distal marker is partially fused together with the distal marker carrier 10. It is also conceivable to embed or swage the distal marker 26 into the distal marker carrier 10 because the material used for the distal marker carrier 10 is relatively soft, preferably a resin tube.

The distal marker carrier 10 is a polymeric tube whereas the pusher element 8, the transfer shaft 12, and rod 16 or tube 16 are made of metal, conveniently stainless steel. It is also conceivable to use other material combinations for these parts, such as nickel titanium shape memory alloy for the transfer shaft 12 and a composition of platinum/iridium (90/10) for the pusher element 8.

The outer sheath 4 may also carry a marker band such as one 27 on its inner luminal surface just proximal of its tapered tip 4A for marking the distal end of the outer sheath 4.

Some applications require a thicker guidewire 2, such as a 35 thou guidewire. In such cases, one may choose to omit the distal marker carrier 10. Otherwise, one may choose to locate the marker 26 distal of the distal end of the stent in the free volume 40 between the stent and the tip 4A, thereby minimising the consumption of lumen cross-section inside the stent lumen. The remaining structure of the pusher assembly can remain the same. Hence the versatility of the pusher assembly is increased because of its usefulness with guidewires of different diameters.

FIG. 3 shows an isometric view of the adapter 20, preferably made of metal, such as stainless steel, effecting the rapid exchange configuration. The adapter comprises two lumens 22, 24 one of which is a guidewire lumen 22 and the other one of which permits the rod 16 or tube to exit the adapter. Lumen 24 of the adapter is defined by two opposing arcuate segments 23A and 23B. The pipe 18 is introduced into lumen 24 of the adapter 20 from the proximal end of the adapter which has the shape of a mushroom until it abuts the distal end of a recess (not shown). In this manner, the adapter does not need to have a circumferential side wall which encloses lumen 24 by 360°. Hence, the lateral dimensions are minimised. Furthermore, as shown in FIG. 3, tension pins (studs) 20A are provided on the outer circumferential surface of the distal portion of the adapter 20 engaging with the braid 43 which is encapsulated by the polymeric material of the outer sheath 4. Lumen 24 which is a guidewire lumen is located off-centre of the adapter 20 and allows the guidewire 2 to exit the delivery system to effect the rapid-exchange configuration. The adapter is preferably made of metal, such as stainless steel, but the use of other alloys is conceivable.

Figure 4:
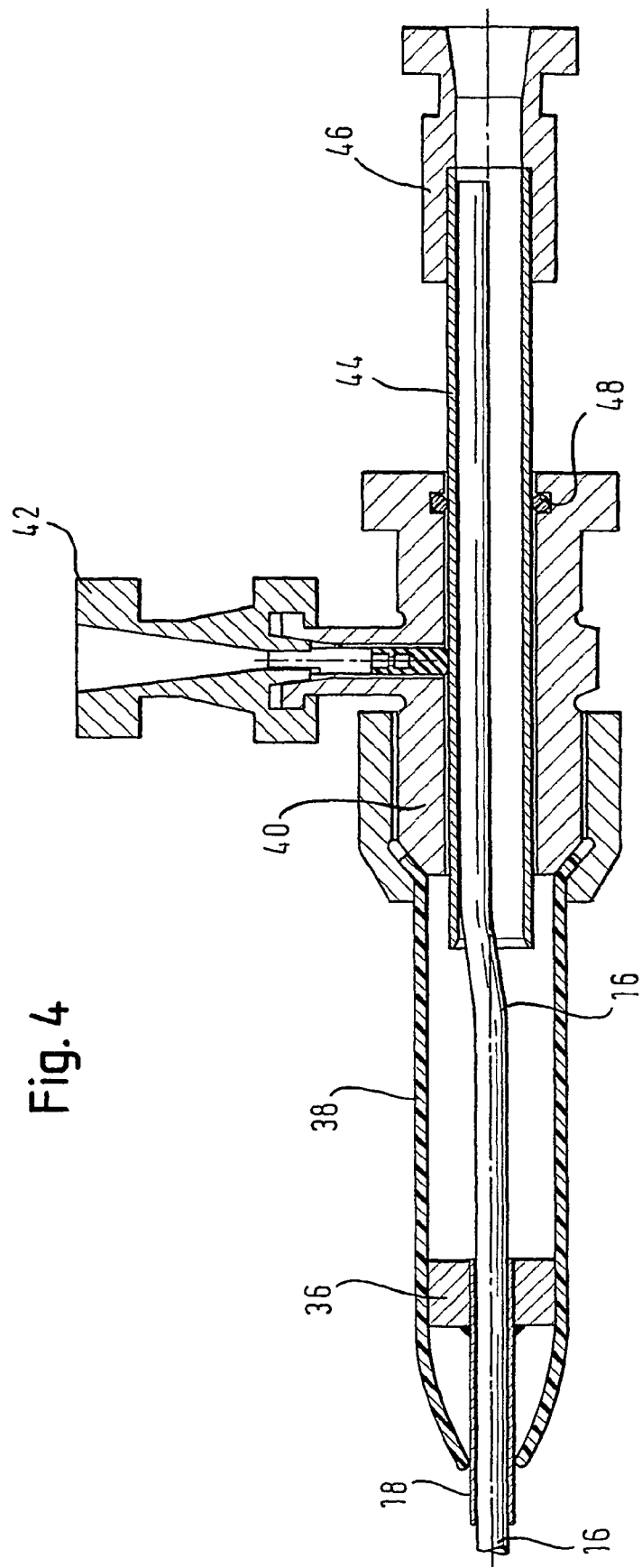
FIG. 4 shows a cross-section of the proximal portion of the delivery system, the pull-back device used to proximally retract the outer sheath, in accordance with a preferred embodiment of the present invention.

Referring now to FIG. 4, a cross-sectional view of the proximal portion of the stent delivery system is shown. The proximal portion is part of a pull-back device used for proximally retracting the outer sheath 4 to release the stent 6. The pipe 18 which is connected to the sheath 4 via the adapter 20 is linked to an adapter ring 36. A welded joint is preferably be used for the link but other types of joints may be used, such as glue or an interference fit etc. The adapter ring 36 is joint to a polymeric sleeve 38 fitted into the distal portion of a distal hub 40. As the distal hub is successively pulled back proximally with every squeeze on the trigger of the pull-back device (not shown), a proximal hub 46 at the proximal end of the rod 16 or tube is held stationary at the same time by a compressive force being transmitted from the proximal hub 46 via rod 16 and transfer shaft 12 to the pusher element 8. In this way, controlled release of the stent at a desired position inside the patient's body is achieved.

The proximal portion of the stent delivery system further provides the possibility to insert contrast fluid through the Luer-adapter 42 into the annulus between the distal hub 40 and a supporting member 44 being sealed by an O-ring 48 and connected to rod 16. The contrast fluid passes beyond the distal end of the distal hub 40, creeps through the gap between the adapter ring 36 and the rod 16 and emerges from the distal end of the pipe 18 finally to reach the distal end of the outer sheath 4 to get squirted out into the vessel of the patient's body.

The Luer-valve assembly 42 also comprises a safety lock for locking the axial movement of rod 16, (the subject of Applicant's PCT/EP02/06782 and earlier British Patent Application No. 0114939.2), which ensures safe transport of the packaged delivery system without the risk of inadvertent release of the stent and to enable the physician to interrupt the stent deployment process, when needed, without having to be concerned with the displacement of the stent whilst the physician is not holding the delivery system in his/her hands.

Figure 5:
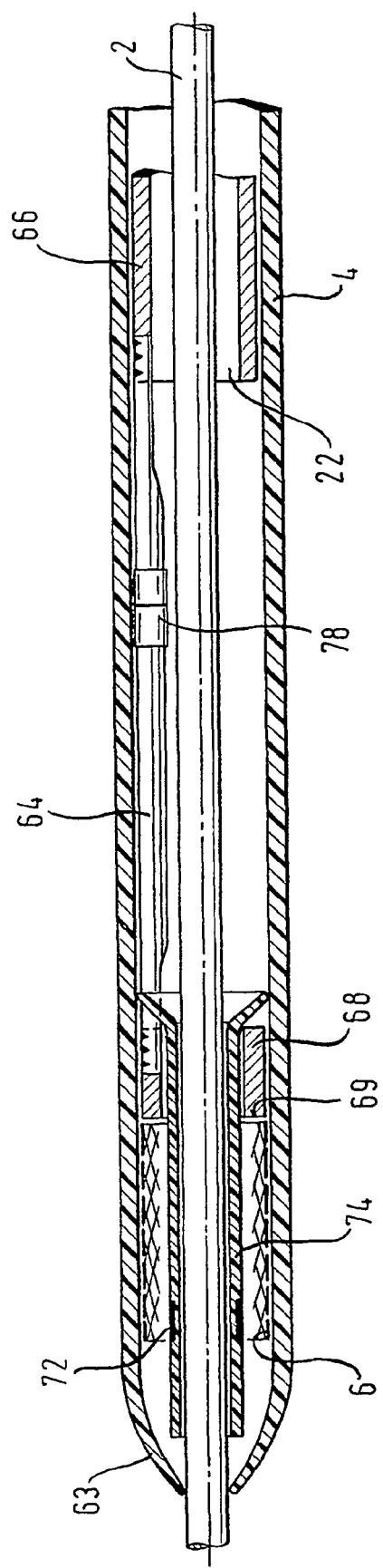
FIG. 5 shows a cross-sectional view of the distal portion of an over-the-wire pusher assembly according to a second embodiment of the invention.

The pusher assembly, as shown in FIG. 5, is destined to be used for an 18 thou guidewire 20. The entire pusher assembly is enclosed by an outer catheter 4 of an over-the-wire stent delivery system prior to deployment of the stent 6. In this condition the stent 6 is held in a radially compressed configuration by the same outer catheter 4. For deployment of the stent 6, the outer catheter 4 is withdrawn until the distal tip 63 is proximal of the proximal end of the stent 6.

The pusher assembly incorporates a catheter shaft 66, the distal end of which is connected to a transfer shaft 64. A pusher element 68 is connected to the distal end of the transfer shaft 64. During the course of stent deployment the distal end 69 of the pusher element 68 abuts the proximal end of the stent 6. Thus, the pusher element 68 serves as a stop for the stent 6 during stent deployment, to prevent proximal movement of the stent as the outer catheter 4 is withdrawn proximally.

The proximal end of the pusher element 68 is laser-welded to the distal end of the transfer shaft 64 and the same manner of connection is used for connecting the proximal end of the transfer shaft 64 to the distal end of the catheter shaft 66.

For ease of connection, both the distal and the proximal ends of the transfer shaft are tapered and embedded in respective slots provided in the proximal end of the pusher element 6 and the distal end of the catheter shaft 66. The ends of the transfer shaft 64 are tapered such that the circular cross-section of the transfer shaft 64 between its ends is oblate at its ends, so that both ends can be fitted into respective slots of the adjacent pusher element 68 and catheter shaft 66, with the circumferential surfaces over a specific arc length of both oblated ends being flush with the circumferential surface of the pusher element 68 and the catheter shaft. The slot provided in the proximal end of the pusher element 68 has an axial length which extends from the proximal end of the pusher element beyond mid-way along the axial length of the pusher element 68. The length of the slot in the distal end of the catheter shaft 66 is much the same length, and long enough to ensure that a sufficient connection between the transfer shaft 64 and the catheter shaft 66 is obtained. Such shaping of the two ends of the transfer shaft and the pusher element 68 and the catheter shaft 66 maximises the flow of injected contrast fluid, since the fluid does not meet any unnecessary barrier when travelling along the length of the transfer shaft. In other words, the resistance to the flow of the injected contrast fluid is minimised.

A connection piece such as a tube 78 at an intermediate position of the transfer shaft 64 enables the accommodation of different stent lengths in an unchanged sheath 4 and catheter shaft 66, by an appropriate adjustment in the length of the transfer shaft portions in accordance with the length of the respective stent. The two cut-to-length transfer shaft portion ends bridged by the connection tube 78 are either glued or soldered to the connection tube 78. The connection tube 78 can be no more than a collar into which the two adjacent ends of the separate transfer shaft portions are inserted and approximated, such that both ends of the transfer shaft are in physical contact with each other inside the collar. Therefore, there is no relative axial movement of the two adjacent ends of the transfer shaft portions within the collar.

A distal marker carrier 74, itself carried on the pusher element 68, exhibits a length sufficient to project distally beyond the stent 6 and defines a lumen for the guidewire 20. In use, the guidewire 20 extends along an axial path which lies side-by-side with the transfer shaft 64 which is off the axis of the outer sheath 4. The proximal end of the distal marker carrier 74 is attached, conveniently by glue, to the inner surface of the pusher element 68 to fix its axial position. The proximal end of the distal marker carrier 74 has a flared end or shows some sort of tulip-shape for undisturbed distal advancement of the guidewire 20 through the pusher assembly of the delivery system. The fixing established by the glue and the flared end also reduces the likelihood of separation of the carrier tube 74 from the pusher element 68. The distal marker carrier 74 carries a distal marker, such as a radiopaque marker 72, indicating the position of the distal end of the stent.

The distal marker carrier 74 is a polymeric tube whereas the pusher element 68, the transfer shaft 64, the catheter shaft 66 and the connection tube 78 are made of metal, conveniently stainless steel. It is also conceivable to use other material combinations for these parts, such as nickel titanium shape memory alloy for the transfer shaft and a composition of platinum/iridium (90/10) for the pusher element 68.

The distal marker 72 can be embedded or swaged into the distal marker carrier 74 because the material used for the distal marker carrier 74 is relatively soft, preferably a resin tube.

Figure 6:
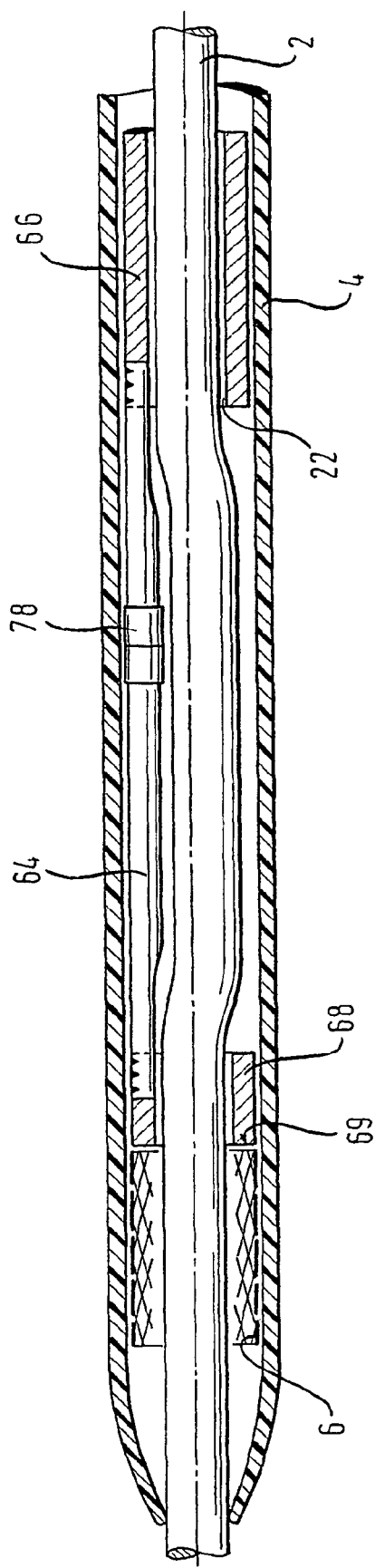
FIG. 6 shows a cross-sectional view of the distal portion of another over-the-wire pusher assembly according to a third embodiment of the invention.

Some applications require a thicker guidewire 20, such as a 35 thou guidewire. In such cases, the distal marker carrier 74 may need to be omitted, as shown in FIG. 6. The remaining structure of the pusher assembly can remain the same. Hence, the versatility of the pusher assembly is increased because of its usefulness with guidewires of different diameters.

Reverting to the embodiment shown in FIG. 5, however, a thicker guidewire can be accommodated if the distal marker 72 is moved to a position just distal of the distal end of the compressed stent 6. To resist bowing of the pushing wire 64, it can be bonded to an additional short length of tube mounted distally to the catheter shaft 66. The bonding could be with glue. The mounting could be a telescopic mounting within the distal open end of the shaft 66, the tube length glued to the said distal end and extending, cantilevered, distal of the distal end with the pushing wire glued to its outside cylindrical surface. Denial of bowing of the pushing wire within the lumen of the outer catheter should eliminate any substantial "lost motion" when the outer catheter is initially pulled back proximally, and the pushing wire 64 goes into compression, in the initial stages of stent release.

Figure 7:
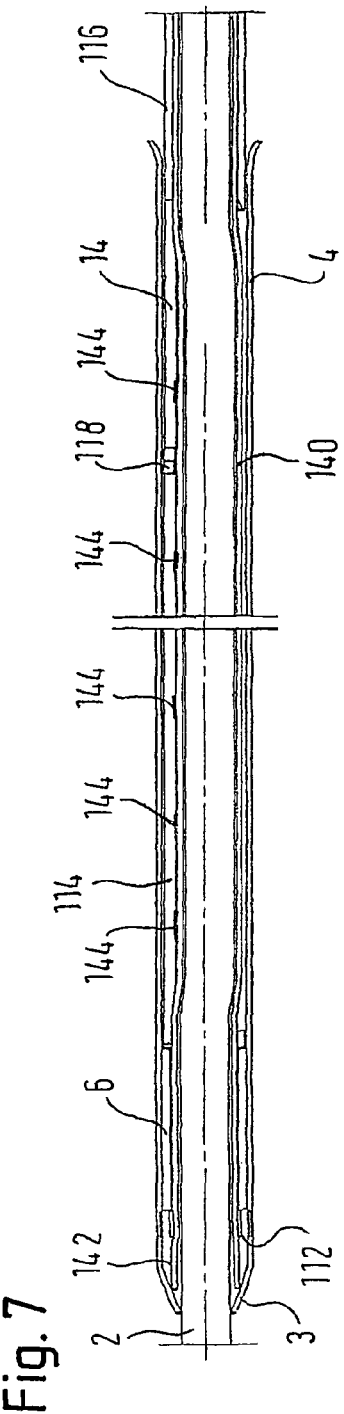
FIG. 7 shows a cross-sectional view of the distal portion of yet another over-the-wire assembly, being a fourth embodiment of the invention.
Figure 8:
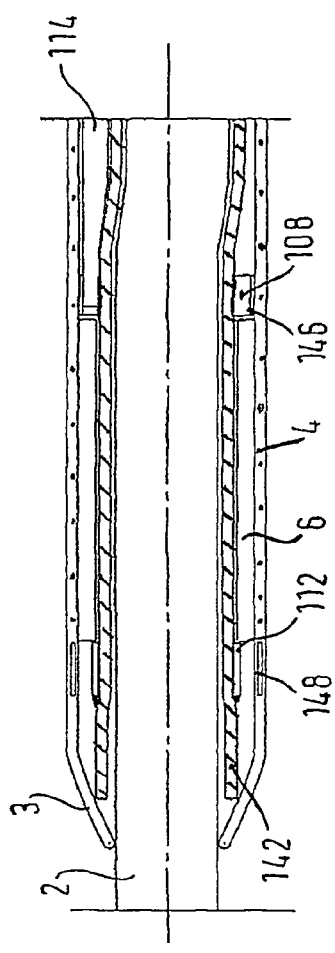
FIG. 8 shows at larger scale the distal tip portion of the FIG. 7 embodiment.
Figure 9:
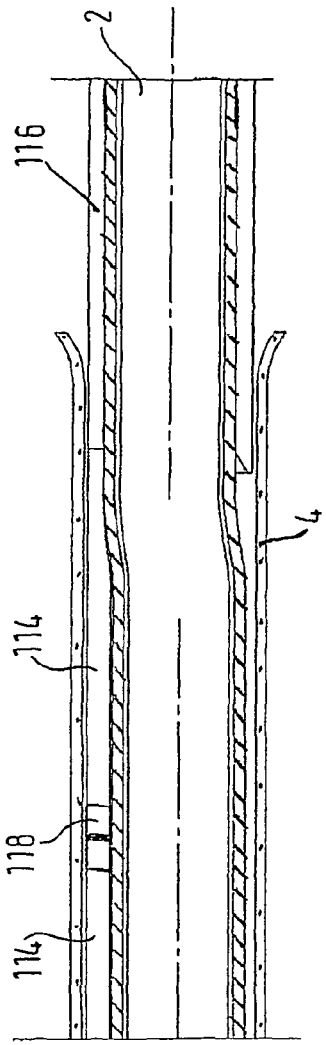
FIG. 9 shows at the scale of FIG. 8 a part of the FIG. 7 distal portion which is proximal of the tip shown in FIG. 8.

Drawing FIGS. 7, 8 and 8 show another embodiment of the invention which is, in some respects, a hybrid of the embodiments of FIGS. 5 and 6.

In FIG. 7 there is an inner catheter 140 of polymeric material, glued inside the stainless steel shaft 116 and extending distally to a distal tip zone 142 which lies distal of the stent 6. Swaged around this distal tip zone is a distal marker 112, lying just distal of a distal end of the stent 6. For the remaining distal tip portion 142 of the inner catheter 140, lying distal of the distal marker 112, the diameter is slightly increased, as can best be seen in FIG. 8, which increases the security with which the marker 112 is retained on the inner catheter shaft 140, with corresponding reduced likelihood of loss of the marker 112 by slipping off the distal end of the catheter 140. As can be seen, the guidewire 20 extends through the shaft 116 and inner catheter 140, being a relatively snug fit within this lumen.

Lying on the outside cylindrical surface of the inner catheter 140 is a transfer shaft 114 and connector 118. With a sequence of glue spots 144, the transfer shaft 114 is bonded to the inner catheter shaft 140, thereby preventing any tendency for the transfer shaft 114 to bow when it is put in longitudinal compressive tension for release of the stent 6.

As shown in FIG. 8, at the distal end of the transfer shaft 14 is the pusher 108 and this carries, on its outside cylindrical surface, an additional thin platinum/iridium radiopaque marker band 146. A further marker 148 is integrated in the thickness of the outer catheter wall 4, just distal of the stent 6, overlying the marker 112 on the inner catheter 140. During progressive deployment of the stent, by proximal withdrawal of the outer catheter 4, the radiologist will be able to observe the progressive movement of the outer catheter marker 48, proximally away from the distal stent marker 112 and towards through and beyond the proximal marker 146.

In the following, some of the advantages of the subject pusher assembly are elucidated.

Since the catheter shaft tube 116, the pusher element 108 and the guidewire 20 are all of metal, friction between the guidewire and the stent delivery system is low, and so PTFE or other special low-friction coatings can be omitted, thereby saving manufacturing costs.

During release of the stent, the transfer shaft remains under a more or less constant compressive strain once it has undergone a certain amount of bowing within the lumen of the outer catheter sheath 4 as a result of the proximal withdrawal of the outer sheath. This bowing typically reduces the distance between the pusher element 108 and the catheter shaft 114 by approximately 5 mm. The compressive strain suffered by the transfer shaft 14 remains constant throughout the deployment of the stent for as long as the outer catheter 4 is in axial tension. Hence, a precise placement of the stent with respect to the stenting site can be achieved and no significant "breathing", as mentioned above, to be observed.

The simplified internal structure of the distal portion of the delivery system enables improved visualisation of the stenosis due an increased volume flow of contrast fluid with each pulse.

During release of the stent, virtually no proximal movement of the stent is seen, while the outer sheath is being withdrawn proximally. The present invention provides a metal structure all the way from the proximal end of the pull back unit receiving the endwise compressive force to the pusher element to keep the stent in place during stent deployment. Therefore, no adverse bowing of the force transmitting components is caused during stent release. Furthermore, the component that is withdrawn proximally, including the outer sheath 4, can also exhibit metal-to-metal connections end-to-end.

As shown in the illustrated embodiments, the length of the transfer shaft, which preferably amounts to a maximum of 3 cm, is relatively short compared to its diameter, so that appreciable bowing is suppressed. In addition, the transfer shaft confined by the outer sheath and lying side-by-side to the guidewire inside the lumen of the outer sheath has nowhere to go when it seeks to bend under compression during stent release, thereby preventing shortening of the distance between the pusher element and the distal end of the rod. Hence, more precise placement of the stent with respect to the stenting site can be achieved. Furthermore, assembly of the system is facilitated and manufacturing cost are reduced.

The system is further adaptable to guidewires of different diameters, which enhances the versatility of the system and its acceptability to the practitioner.

The delivery system may be used in connection with a guiding catheter. The physician attempting to bring a stent to a stenosis site inside the patient's body uses an outer guide catheter to be first introduced in the patient's body. Once the guide catheter has been properly placed, a guidewire is introduced through the guide catheter lumen along which the delivery system is advanced to the site of the stenosis in a next step. Here, the contrast fluid to be used to visualise the stenosis can be injected, if the physician prefers to do so, through the gap between the internal surface of the guide catheter and the external surface of the delivery system. Hence, the annulus between the pipe 18 and the rod 16 or tube, shown in FIG. 2, can be further reduced in order to minimise the transverse dimension of the delivery system, which is advantageous in terms of both, the recovery of the patient and the handling comfort for the physician.

Prior to use of the delivery system, as is the case for any devices used to inject fluids into the human body, the delivery system needs to be vented and primed, i.e. the system is flushed with a biocompatible solution, such as a sodium chloride solution, until all the air confined inside the system has been driven out of the system. The delivery system of the present invention may be flushed with such a solution from the distal tip of the delivery system prior to use. This may enhance the practical usefulness of the delivery system, since the guidewire is also inserted into the delivery system from the distal end of the system, so that the physician can carry out the flushing and the guidewire insertion almost in one go. This allows the physician to choose the alternative with which he/she has grown most comfortable and which is best suited for the specific circumstances.

The invention claimed is:

1. A pusher assembly for a delivery system for a self-expanding stent, the pusher assembly constituting a catheter shaft with a proximal pusher end to receive an end-wise compressive force and a distal pusher end to deliver said force to a stent to be delivered, the pusher assembly comprising:
   a pusher strand extending from the proximal pusher end to a distal strand end which is nearer the distal pusher end than the proximal pusher end;
   a pusher element which abuts the stent in use to deliver said force to the stent; and
   a transfer shaft having a length with a proximal end and a distal end, the transfer shaft tapering distally along at least a portion of the length toward the transfer shaft distal end, the transfer shaft proximal end being connected to the distal strand end and the transfer shaft distal end being connected to the pusher element; and
   the pusher element defines a guidewire path, and said transfer shaft lies to one side of said path but is not coaxial with said path.

2. The pusher assembly according to claim 1, wherein the transfer shaft is welded to at least one of the pusher element and the pusher strand.

3. The pusher assembly according to claim 1, wherein the pusher element is a cylinder with a distal-facing end face to abut a proximal end of the stent.

4. The pusher assembly according to claim 1, wherein the pusher element is a radiopaque marker.

5. The pusher assembly according to claim 1, further comprising a carrier tube, the pusher element surrounds the carrier tube, the carrier tube being carried on the pusher element and cantilevered distally from the pusher element to lie within a lumen of the stent to be delivered.

6. The pusher assembly according to claim 5, further comprising a radiopaque marker on the carrier tube for marking a distal end of the stent.

7. The pusher assembly according to one of claim 5 or 6, wherein a proximal portion of the carrier tube extends proximally from the pusher element and flares outwardly proximally.

8. The pusher assembly according to claim 1, in which the transfer shaft has a first transfer shaft portion and a second shaft portion joined together by a connection piece.

9. The pusher assembly according to claim 8, wherein the connection piece is a collar.

10. The pusher assembly according to one of claim 8 or 9, wherein each of the transfer shaft portions is soldered to the connection piece.

11. A self-expanding stent deployment system for advancement over a guidewire and having a rapid exchange configuration, comprising:
   a tubular sheath defining a cavity within which a stent is confined in a radially inwardly position until deployment, the sheath having a distal end and a proximal end and defining an axis of the system;
   a pipe to pull the sheath proximally to release the stent and having a lumen to transport fluid for delivery to the sheath cavity;
   a pusher assembly including:
      a pusher strand extending from a proximal end of the system to a distal end of the system;

a pusher element which abuts the stent in use; and a transfer shaft having a length with a proximal end and a distal end, the transfer shaft tapering distally along at least a portion of the length toward the transfer shaft distal end, the transfer shaft proximal end being connected to a distal end of the pusher strand and the transfer shaft distal end being connected to the pusher element, the pusher element defines a guidewire path, and said transfer shaft lies to one side of said path but is not coaxial with said path;

an adapter defining at least first and second lumens arranged side by side and parallel with the axis of the system and arranged to transmit forces between the sheath and the pipe, wherein the first lumen is a guidewire lumen, and the second lumen communicates with the lumen of the pipe and with the sheath cavity, and the sheath having a tapered tip disposed distal of the stent cavity which enables the guidewire to pass distally beyond the distal end of the sheath.

12. The system according to claim 11, further comprising the pusher element is a cylinder with a distal-facing end face to abut a proximal end of the stent.

13. The system according to claim 11, wherein the pusher element constitutes a radiopaque marker.

14. The system according to claim 11, wherein the transfer shaft is welded to at least one of the pusher element and the pusher strand.

15. The system according to claim 11, wherein the transfer shaft comprises two shaft portions joined by a connection piece.

16. The system according to claim 15, characterized in that the connection piece is a collar.

17. The system according to claim 15, characterized in that each of the transfer shaft portions is soldered to the connection piece.

18. The system according to claim 11, wherein the adapter is made of metal.

19. The system according to claim 11, wherein the connection between the sheath and the adapter is made by means of an adhesive.

20. The system according to claim 11, wherein the sheath comprises an encapsulated metal braid.

21. The system according to claim 20, further comprising metal studs disposed around a circumferential surface of a distal end of the adapter, the studs cooperatively engaging the metal braid.

22. The system according to claim 11, wherein the first lumen is defined by two arcuate segments.

23. The system according to claim 11, wherein the pipe is inserted into the second lumen of the adapter until it abuts an end face of a recess provided on the defining walls of the second lumen.

24. The system according to claim 11, further comprising a carrier tube, the pusher element surrounds the carrier tube, the carrier tube being carried on the pusher element and cantilevered distally from the pusher element to lie within a lumen of the stent to be delivered.

25. The system according to claim 24, wherein the carrier tube itself carries a radiopaque marker marking a distal end of the stent.

26. The system according to claim 24, wherein a proximal portion of the carrier tube extends proximally from the pusher element and flares outwardly proximally.

27. A pusher assembly for maintaining the position of a stent, comprising:

a carrier tube disposed within the stent and defining a longitudinal axis, the carrier tube having a proximal end;

a pusher element having proximal and distal surfaces, the distal surface abutting the stent, the proximal and distal surfaces defining an inner passage through the pusher element, the proximal end of the carrier tube disposed within the inner passage; and a transfer shaft having a length and proximal and distal ends, the transfer shaft distal end abutting the proximal face of the pusher element, the transfer shaft extending proximally from the proximal surface of the pusher element in a direction that is offset from but parallel to the longitudinal axis, the transfer shaft tapering distally along at least a portion of the length toward the transfer shaft distal end.

\* \* \* \* \*